(12) United States Patent
Sams et al.

(10) Patent No.: US 9,546,997 B2
(45) Date of Patent: Jan. 17, 2017

(54) STRIP GRABBER

(71) Applicant: BAYER HEALTHCARE LLC, Whippany, NJ (US)

(72) Inventors: Robert S. Sams, Pittsfield, MA (US); Eugene Prais, West Milford, NJ (US); Simin Yao, Boonton Township, NJ (US)

(73) Assignee: Ascensia Diabetes Care Holdings AG, Basel (CH)

( * ) Notice: Subject to any disclaimer, the term of this patent is extended or adjusted under 35 U.S.C. 154(b) by 0 days.

(21) Appl. No.: 14/774,118

(22) PCT Filed: Mar. 11, 2014

(86) PCT No.: PCT/US2014/023266
§ 371 (c)(1),
(2) Date: Sep. 9, 2015

(87) PCT Pub. No.: WO2014/164705
PCT Pub. Date: Oct. 9, 2014

(65) Prior Publication Data
US 2016/0018385 A1 Jan. 21, 2016

Related U.S. Application Data

(60) Provisional application No. 61/776,506, filed on Mar. 11, 2013.

(51) Int. Cl.
*B65H 5/00* (2006.01)
*G01N 33/487* (2006.01)

(52) U.S. Cl.
CPC .... *G01N 33/48757* (2013.01); *G01N 33/4875* (2013.01)

(58) Field of Classification Search
CPC ................ G01N 33/4875; G01N 33/48757
See application file for complete search history.

(56) References Cited

U.S. PATENT DOCUMENTS

| | | |
|---|---|---|
| 2,944,661 A | 7/1960 | Goldstein |
| 3,194,426 A | 7/1965 | Brown |
| 3,592,356 A | 7/1971 | Rovin |
| 3,651,585 A | 3/1972 | Perrella et al. |
| 3,717,282 A | 2/1973 | Nordskog |
| 4,218,421 A | 8/1980 | Mack, Jr. et al. |
| 4,705,331 A | 11/1987 | Britton |
| 4,721,677 A | 1/1988 | Clark |

(Continued)

FOREIGN PATENT DOCUMENTS

| | | |
|---|---|---|
| WO | WO 2010/065307 | 6/2010 |
| WO | WO 2010/065309 | 6/2010 |
| WO | WO 2012/064645 A2 | 5/2012 |

OTHER PUBLICATIONS

International Search Report and Written Opinion of International Application No. PCT/US2009/64949 dated Jan. 13, 2010.

(Continued)

*Primary Examiner* — Howard Sanders
(74) *Attorney, Agent, or Firm* — Dugan & Dugan, PC

(57) ABSTRACT

The present disclosure relates to a test strip handling device (100) that includes a housing (110) having an interior compartment (112) in which the test strips are received and stored. The device (100) facilitates sanitary handling and disposal of the test strips.

20 Claims, 5 Drawing Sheets

(56) References Cited

U.S. PATENT DOCUMENTS

| | | |
|---|---|---|
| 4,771,887 A | 9/1988 | Nehl |
| 5,314,825 A | 5/1994 | Weyrauch et al. |
| 5,335,816 A | 8/1994 | Kaufman et al. |
| 5,335,822 A | 8/1994 | Kasper |
| 5,375,920 A | 12/1994 | Macchi |
| 5,609,823 A | 3/1997 | Harttig et al. |
| 5,846,486 A | 12/1998 | Pugh |
| 5,854,074 A | 12/1998 | Charlton et al. |
| 5,856,195 A | 1/1999 | Charlton |
| 6,036,924 A | 3/2000 | Simmons |
| 6,099,802 A | 8/2000 | Pugh |
| 6,130,263 A | 10/2000 | Hekal |
| 6,136,352 A | 10/2000 | Silverstein et al. |
| 6,170,230 B1 | 1/2001 | Chudy et al. |
| 6,378,702 B1 | 4/2002 | Kintzig |
| 6,625,952 B1 | 9/2003 | Chudy et al. |
| 6,827,899 B2 | 12/2004 | Maisey |
| 6,881,578 B2 | 4/2005 | Otake |
| 6,908,008 B2 | 6/2005 | Pugh |
| 6,997,343 B2 | 2/2006 | May |
| 7,138,089 B2 | 11/2006 | Aitken |
| 7,264,139 B2 | 9/2007 | Brickwood et al. |
| 7,270,247 B2 | 9/2007 | Charlton |
| 7,501,093 B2 | 3/2009 | Demelo et al. |
| 7,552,843 B2 | 6/2009 | Kuriger et al. |
| 7,638,095 B2 | 12/2009 | Sabol |
| 7,723,113 B2 | 5/2010 | Charlton |
| 7,875,243 B2 | 1/2011 | Rush et al. |
| 8,236,254 B2 | 8/2012 | Myles et al. |
| 8,388,905 B2 | 3/2013 | Neel et al. |
| 8,684,172 B2 | 4/2014 | Yao |
| 8,691,161 B2 | 4/2014 | Fleming |
| 8,940,540 B2 | 1/2015 | Charlton et al. |
| 9,097,699 B2 | 8/2015 | Charlton et al. |
| 2002/0057993 A1 | 5/2002 | Maisey et al. |
| 2002/0076349 A1 | 6/2002 | Aitken et al. |
| 2003/0089730 A1 | 5/2003 | May et al. |
| 2003/0116583 A1 | 6/2003 | Pugh |
| 2003/0175155 A1 | 9/2003 | Charlton |
| 2003/0191415 A1 | 10/2003 | Moerman et al. |
| 2003/0211616 A1 | 11/2003 | Leong |
| 2003/0223906 A1 | 12/2003 | McAllister |
| 2004/0007585 A1 | 1/2004 | Griffith et al. |
| 2004/0178216 A1 | 9/2004 | Brickwood et al. |
| 2005/0142363 A1 | 6/2005 | Noda |
| 2006/0076236 A1 | 4/2006 | Shah et al. |
| 2006/0076358 A1 | 4/2006 | Shigeyama et al. |
| 2006/0191813 A1 | 8/2006 | Yamaoka |
| 2006/0266765 A1 | 11/2006 | Pugh |
| 2007/0125677 A1 | 6/2007 | Oronsky et al. |
| 2007/0183925 A1 | 8/2007 | Schabbach |
| 2007/0189928 A1 | 8/2007 | Sabol |
| 2007/0196240 A1 | 8/2007 | Boozer |
| 2007/0264165 A1 | 11/2007 | Chan et al. |
| 2008/0007141 A1 | 1/2008 | Deck |
| 2008/0094804 A1 | 4/2008 | Reynolds et al. |
| 2008/0108130 A1 | 5/2008 | Nakaminami |
| 2008/0131322 A1* | 6/2008 | Kheiri .............. G01N 33/48757 422/82.01 |
| 2008/0164280 A1 | 7/2008 | Kuriger et al. |
| 2008/0181818 A1 | 7/2008 | Ruan |
| 2008/0257905 A1 | 10/2008 | Giraud et al. |
| 2008/0286149 A1 | 11/2008 | Roe et al. |
| 2009/0095071 A1 | 4/2009 | Wu et al. |
| 2010/0041156 A1 | 2/2010 | Brenneman et al. |
| 2011/0073476 A1 | 3/2011 | Gofman et al. |
| 2011/0226643 A1 | 9/2011 | Kates et al. |
| 2013/0324822 A1 | 12/2013 | Prais et al. |
| 2014/0054169 A1 | 2/2014 | Gofman et al. |
| 2014/0273041 A1 | 9/2014 | Charlton |
| 2015/0004059 A1 | 1/2015 | Brown et al. |

OTHER PUBLICATIONS

International Preliminary Report on Patentability of International Application No. PCT/US2009/64949 dated Jun. 16, 2011.
International Search Report and Written Opinion of International Application No. PCT/US2009/64963 dated Mar. 4, 2010.
International Preliminary Report on Patentability of International Application No. PCT/US2009/64963 dated Jun. 16, 2011.
International Search Report and Written Opinion of International Application No. PCT/US2014/023266 mailed Jun. 16, 2014.
International Preliminary Report on Patentability of International Application No. PCT/US2014/023266 mailed Sep. 24, 2015.
Taiwan Search Report of Taiwan Application No. 103108342 dated Jun. 1, 2015.
European Extended Search Report of European Application No. 14779994.4 dated Oct. 7, 2016.

* cited by examiner

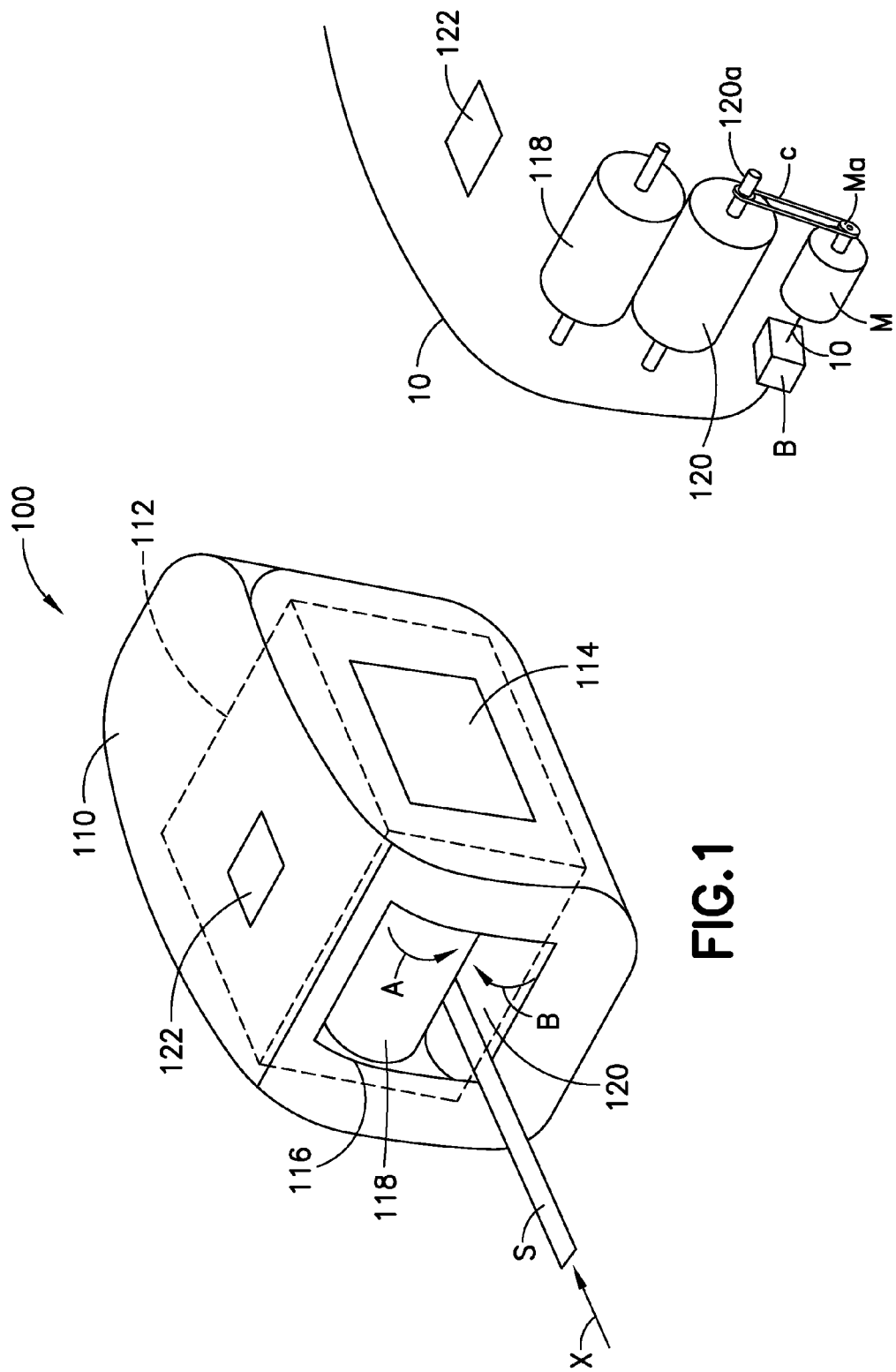

STRIP GRABBER

CROSS-REFERENCE TO RELATED APPLICATIONS

The present application claims the benefit of the filing date of U.S. Provisional Patent Application No. 61/776,506 filed Mar. 11, 2013, the disclosure of which is hereby incorporated herein by reference.

BACKGROUND OF THE INVENTION

The present disclosure generally relates to the collection, handling, and/or disposal of items. More particularly, the present disclosure relates to the collection, handling, and/or disposal of thin strips of material such as reagent test strips.

The detection of a wide range of analytes present in bodily fluid is necessary for the detection, management, and treatment of many different medical conditions. The quantitative determination of analytes in body fluids is of great importance in the diagnosis and maintenance of certain physiological conditions. For example, certain diabetic individuals require frequent testing of their blood glucose levels to regulate the glucose intake in their diets. The results of such tests can be used to determine what, if any, medication, such as insulin medication, should be administered.

Traditionally, the detection of analytes in a body fluid, such as blood, saliva, or urine, was performed in a laboratory by trained technicians. Increasingly, however, fluid analyte systems that provide for rapid and point-of-care testing are being used. These fluid analyte systems allow for testing at a patient's bedside without requiring a time consuming and costly laboratory analysis.

Often, these fluid analyte systems utilize test strips that provide an indication of the presence and/or concentration of particular substance within the body fluid being analyzed. The test strips are often thin strips of material, such as paper or plastic, which include one or more pads that are impregnated with a reagent. A reagent is a substance that has a chemical reaction when exposed to a given substance. When the test strip comes in contact with a body fluid, the test strip absorbs the body fluid and if a given substance is present in the body fluid, the reagent reacts with the substance. The reaction of the reagent upon contact with the body fluid provides an indication of the presence and/or concentration of particular substance.

Since used test strips have been exposed to potentially dangerous bodily fluids, proper handling and disposal to minimize the likelihood of unprotected exposure are desirable. A continuing need exists for devices that facilitate sanitary handling and disposal of used test strips.

BRIEF SUMMARY OF THE INVENTION

In an embodiment of the present disclosure, a test strip handling device may include a housing and an inner compartment within the housing. The inner compartment may have a space in which at least one item may be stored. The housing may include an opening that is connected to the space of the inner compartment. The device may further include a first member and a second member that are configured to securely receive the at least one item therebetween and to guide the at least one item through the opening and into the space of the inner compartment. The first and second members may inhibit removal of the at least one item via the opening. A guide channel may be configured to receive the at least one item therethrough to direct the at least one item toward the space of the inner compartment. A door may be formed in the housing through which the at least one item may be removed from the inner compartment.

The first and second members may each be rollers. The first and second rollers may contact each other and/or may frictionally engage one another. The first member may be a roller and the second member may be a roller. The first roller may have a generally cylindrical configuration and may have a first axis extending lengthwise. The second roller may have a generally cylindrical configuration and may have a second axis extending lengthwise. The first and second axes may be generally parallel to one another. The first and second rollers may be rotatable relative to one another. The first and second rollers may be configured to cause translation of the at least one item when the at least one item is positioned between the first and second rollers. An actuator may be configured to cause rotation of the first and second rollers relative to one another.

An energy storage device may bias the first and second rollers to rotate relative one another. The energy storage device may include a third roller, a spring, and a locking mechanism, which may be transitionable between a locked an unlocked state. Rotation of the third roller in a first direction may cause the spring to wind and store potential energy. When the locking mechanism is in the locked state, the spring may be prevented from unwinding, and when the locking mechanism is in the unlocked state, the spring may unwind to convert the potential energy to kinetic energy which may cause the first and second rollers to rotate relative to one another. The locking mechanism may include a pinion that is operatively coupled to at least one of the first and second rollers, and a rack configured to engage the pinion when in the locked state and to be disengaged from the pinion when in the unlocked state.

In another aspect of the presently disclosed embodiments, a test strip handling device can be used to store test strips that include a reagent adapted to react with an analyte in a fluid sample and to produce a reaction indicative of the concentration of the analyte in the fluid sample. The test strip handling device includes a housing having an external opening, an interior compartment, and first and second components. The interior compartment can be disposed within the housing and can include a space in which the at least one test strip may be stored. The first and second members can be positioned adjacent one another within the housing and are constructed and arranged to receive the at least one test strip there between and to guide the at least one test strip from the opening into the space of the interior compartment. In some embodiments, the at least one test strip can be stored within the interior compartment and the first and second members can inhibit removal of the at least one test strip through the opening. A guide channel can be configured to receive the at least one test strip there through in a direction toward the space of the interior compartment.

The first member can be a first roller and the second member can be a second roller. The first roller may have a generally cylindrical configuration and a first axis extending lengthwise. The second roller may have a generally cylindrical configuration and has a second axis extending lengthwise. The first axis and the second axis may be generally parallel with respect to each other.

The first and second rollers may be rotatable relative to one another, and the first and second rollers may be configured to cause translation of the at least one test strip when the at least one test strip is positioned between the first and second rollers. In some embodiment, the first roller is in contact with the second roller. In alternative embodiments, the first roller and the second roller may be spaced apart from one another, such that a gap is created between them. The gap can be sized to receive a test strip therein.

Counter-clockwise rotation of the first roller and clockwise rotation of the second roller can cause translation of the at least one test strip in a direction toward the space of the inner compartment when the at least one test strip is positioned between the first and second rollers.

An actuator can be configured to cause rotation of the first and second rollers relative to one another. An energy storage device can be configured to bias the first and second rollers to rotate relative to one another. In one embodiment, the energy storage device includes a third roller, a spring, and a locking mechanism that is transitionable between a locked state and an unlocked state. Rotation of the third roller in a first direction causes the spring to wind and store potential energy. When the locking mechanism is in the locked state, the spring is prevented from unwinding. Alternatively, when the locking mechanism is in the unlocked state, the spring unwinds to convert the potential energy to kinetic energy, which causes the first and second rollers to rotate relative to one another. In some embodiments, the locking mechanism includes a pinion operatively coupled to at least one of the first and second rollers, and a rack configured to engage the pinion when in the locked state, which is disengaged from the pinion when in the unlocked state.

In another aspect of the present invention, a test strip handling device includes a housing, an interior compartment disposed within the housing, and first and second rollers positioned adjacent one another within the housing and capable of rotating relative to one another. The interior compartment may include a space in which at least one test strip may be stored, the at least one test strip including a reagent adapted to react with an analyte in a fluid sample and to produce a reaction indicative of the concentration of the analyte in the fluid sample. When the at least one test strip is positioned adjacent the first and second rollers, counter-clockwise rotation of the first roller and clockwise rotation of the second roller causes translation of the at least one test strip in a direction toward the space of the interior compartment. The first roller may have a generally cylindrical configuration and a first axis extending lengthwise. The second roller may have a generally cylindrical configuration and a second axis extending lengthwise. The first axis and the second axis may be generally parallel with respect to each other. In some embodiments, the first roller is in contact with the second roller. In other embodiments, the first roller and the second roller are spaced apart from one another, such that a gap is created therebetween, the gap sized to receive the test strip therein. An energy storage device, as previously described in the Summary, can also be used to bias the first and second rollers to rotate relative to one another.

In another aspect, there is a method of storing a test strip that includes a reagent adapted to react with an analyte in a fluid sample and to produce a reaction indicative of the concentration of the analyte in the fluid sample. The method includes: placing an end of the test strip into an opening of a test strip handling device and positioning the test strip at the junction between first and second rollers housed within the test strip handling device, such that the test strip is positioned adjacent the first and second rollers; actuating the first roller to rotate in a first direction and the second roller to rotate in a second direction, wherein the second direction is opposite the first direction; and drawing the test strip into an interior compartment of the test strip handling device while the first and second rollers are rotating. In some embodiments, the step of actuating occurs after the step of placing.

These and other embodiments of the present disclosure are more fully described hereinbelow.

BRIEF DESCRIPTION OF THE DRAWINGS

Various embodiments of the present invention will now be described with reference to the appended drawings. It is appreciated that these drawings depict only some embodiments of the invention and are therefore not to be considered limiting in their scope.

FIG. 1 is a schematic perspective view of an embodiment of a strip handling device in accordance with the present disclosure;

FIG. 2 is a schematic perspective view of the strip handling device of FIG. 1 shown with parts removed;

DETAILED DESCRIPTION

Figure 3:
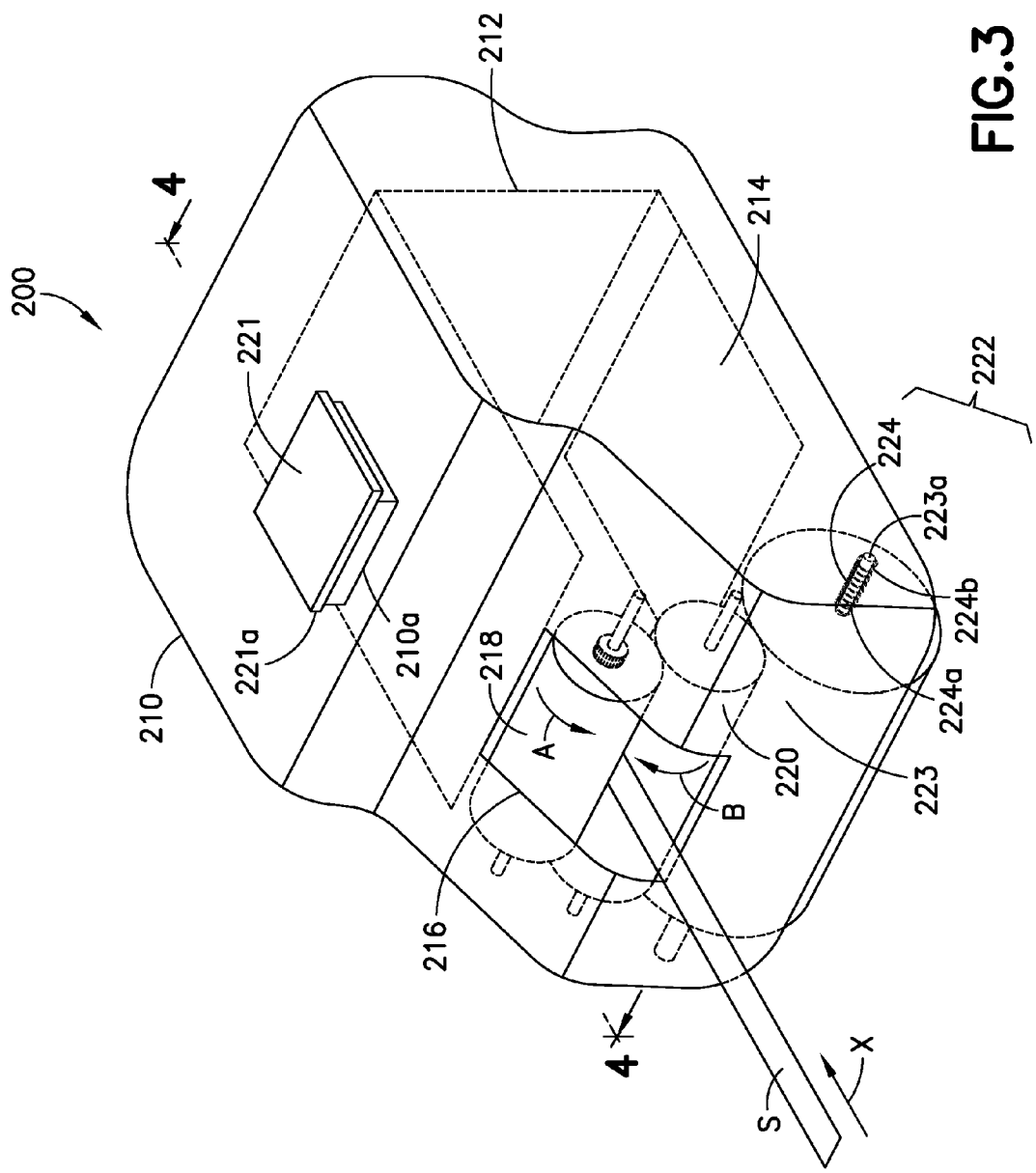
FIG. 3 is a schematic perspective view of another embodiment of a strip handling device in accordance with the present disclosure.

Particular embodiments of the present disclosure are described with reference to the accompanying drawings. In the figures and in the description that follow, like reference numerals identify similar or identical elements.

A test strip handling device 100 will now be described with reference to FIGS. 1 and 2. Test strip handling device 100 may include a housing 110 having an inner compartment 112 therein. Inner compartment 112 defines a space in which one or more strips S may be received and stored. A door 114 may be formed in housing 110 to facilitate access to inner compartment 112 so that the inner compartment may be emptied. A window 116 formed in housing 100 may also provide access to inner compartment 112. A first roller 118 and a second roller 120 may be positioned between window 116 and inner compartment 112 such that the first and second rollers 120 prevent items within the inner compartment from exiting through the window. First roller 118 and second roller 120 in combination may substantially fill the space of window 116 such that items may not pass through the window 116 without passing between the first and second rollers. Rollers 118, 120 may be pivotably coupled to and supported by housing 110 such that the rollers are rotatable, but other movement of the rollers is inhibited.

First and second rollers 118, 120 may be in frictional contact with one another or may have a gap therebetween corresponding to the thickness of strip S. First roller 118 and second roller 120 are rotatable relative to one another. When a strip S is positioned between first roller 118 and second roller 120, the counter rotation of the first and second rollers relative to one another will cause the strip to translate between the first and second rollers.

Depending upon the direction the first and second rollers rotate, strip S will either move in a direction toward inner compartment 112 or in a direction away from the inner compartment. For example, counter-clockwise rotation of first roller 118 as indicated by directional arrow A and clockwise rotation of second roller 120 as indicated by directional arrow B results in translation of strip S toward and into inner compartment 112 as indicated by directional arrow X. An actuator 122 may selectively activate device 100 to cause first roller 118 and second roller 120 to rotate.

With reference to FIG. 2, a motor M, such as an electric motor, may be operatively connected to first roller 118 and second roller 120 such that when motor M is actuated, the first and second rollers will rotate relative to one another. Motor M may have a spindle Ma which extends from the motor and rotates when the motor is being operated. Second roller 120 may have a spindle 120a extending therefrom, the rotation of which will result in the rotation of the second roller. Spindle Ma of motor M and spindle 120a of second roller 120 may be operatively coupled to one another by a cable C such that when the motor is being operated, the second roller will rotate. As second roller 120 rotates, frictional engagement of the second roller with first roller 118 will cause the first roller to rotate in a direction opposite the rotation of the second roller.

Motor M may be electrically connected to a power source B, such as a battery (not shown). Actuator 122 functions as a switch to activate power source B, such as a battery, such that when in an on position power is supplied to motor M and in an off position power is not supplied to the motor. When power is supplied to motor M, the motor will result in the rotation of first and second rollers 118, 120 as described above.

During use, a strip S may extend from a medical device, such as a glucose testing meter (not shown). Removal of strip S may be effectuated by placing an end of the strip in contact with first roller 118 and second roller 120 at the junction of the first and second rollers such that the strip is positioned therebetween. The operator may then cause first roller 118 to rotate in direction A and second roller 120 to rotate in direction B such that strip S is drawn in direction X into inner compartment 112. When inner compartment 112 is full, device 100 may be discarded or otherwise disposed of. Alternatively, inner compartment 112 may be emptied by, for example, opening door 114 and removing the collected strips S from the inner compartment.

Another embodiment of a test strip handling device will now be described with reference to FIGS. 3-6B. A test strip handling device 200 may include a housing 210, which has an inner compartment 212 therein. Inner compartment 212 defines a space in which one or more strips S may be received and stored. A door 214 may be formed in housing 210 to provide access to inner compartment 212 such that the inner compartment may be emptied.

Window 216 may be formed in housing 210 between the exterior of the housing and inner compartment 212. A first roller 218 and a second roller 220 may substantially fill the space of window 216, preventing items from being removed from inner compartment 212 via window 216. First and second rollers 218, 220 may each include a pair of spindles at opposing ends that are pivotably supported by housing 210 such that the rollers are rotatable.

An actuator 221 may be operatively connected to the first and second rollers 218, 220 such that the actuator may cause the first and second rollers to rotate relative to one another. First roller 218 and second roller 220 may be in frictional contact with one another such that rotation of one of the rollers will cause rotation of the other. First roller 218 and second roller 220 may be spaced apart a distance corresponding to the thickness of strip S such that when the strip is positioned therebetween the first and second rollers will frictionally engage with one another. When strip S is positioned between first roller 218 and second roller 220, counter-clockwise rotation of the first roller in direction A and clockwise rotation of the second roller in direction B will cause the strip to translate in direction X toward and into inner compartment 212.

A winding mechanism 222 may include a roller 223 that is supported by housing 210 and a torsion spring 224. Roller 223 may include a spindle 223a, which may be pivotably secured to housing 210 such that roller 223 may rotate. Torsion spring 224 may be positioned on spindle 223a. Torsion spring 224 may include a first end 224a and a second end 224b. First end 224a may be secured to roller 223, and second end 224b may be secured to housing 210. Rotation of roller 223 in a first direction causes torsion spring 224 to wind and store potential energy. Roller 223 may be in frictional engagement with second roller 220, which in turn may be in frictional engagement with first roller 218. Thus, when wound, torsion spring 224 biases first roller 218 to rotate in direction A and second roller 220 to rotate in direction B. When torsion spring 224 is allowed to unwind, the potential energy stored by the wound torsion spring is converted into kinetic energy causing roller 223 to rotate in direction A. Since roller 223 contacts roller 220 causing second roller 220 to move in direction B, which is in an opposite direction to direction A. As second roller 220 rotates, the frictional engagement of the second roller with first roller 218 results in a corresponding rotation of the first roller in direction A.

Figure 4:
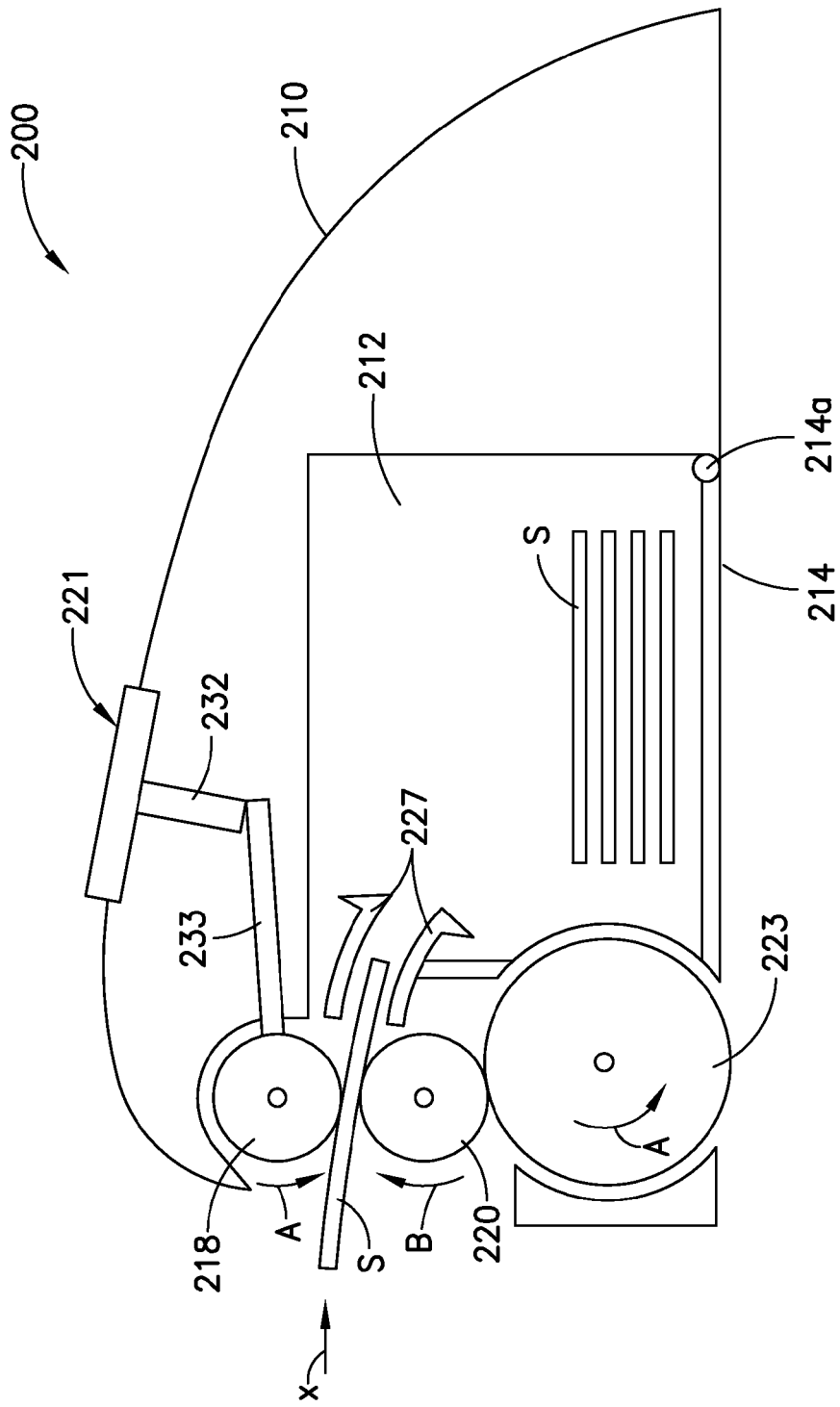
FIG. 4 is a schematic cross-sectional view of the strip handling device of FIG. 3 taken along section line 4-4.

Accordingly, when strip S is positioned between first and second rollers 218, 220, the strip will be drawn toward and into inner compartment 212. As shown in FIG. 4, first and second rollers 218, 220 may draw strip S into a channel defined by the space between a pair of guide members 227, thereby directing the strip into inner compartment 212. The guide members 227 may facilitate predictable placement and stacking of successively received strips S within inner compartment 212. Proper placement and stacking of strips S within inner compartment 212 may facilitate maximization of the number of strips receivable and storable within the inner compartment. Strips S may be removed from inner compartment 212 for disposal by opening door 214, which may be operatively coupled to housing 210 via a hinge 214a.

Figure 5:
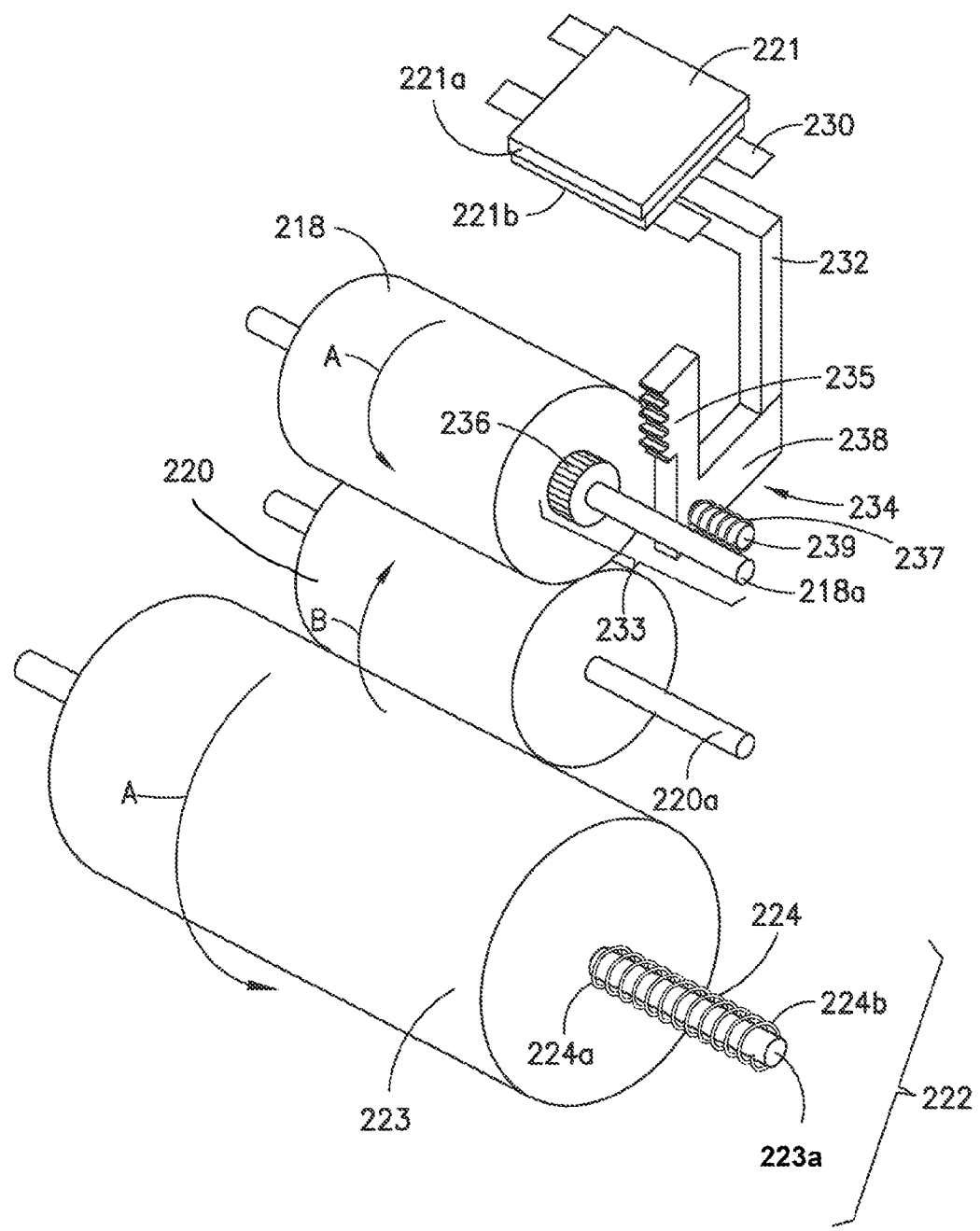
FIG. 5 is a schematic perspective view of the strip handling device of FIG. 3 shown with parts removed.

The selective actuation of strip handling device 200 is described with reference to FIGS. 3 and 5. Actuator 221 may be movable through an opening 210a of housing 210 to selectively actuate a locking mechanism 233. Actuator 221 may have a flanged surface 221a, which is configured to interact with an outer surface of housing 210 such that the actuator may only be depressed a predetermined depth into the housing. Biasing members 230 may be secured to a bottom surface 221b of actuator 221 to bias the actuator toward an undepressed position. Biasing members 230 may be capable of small deflections such that as actuator 221 is depressed depthwise into housing 210, the biasing members are deflected and return the actuator back to its initial undepressed position.

Figure 6B:
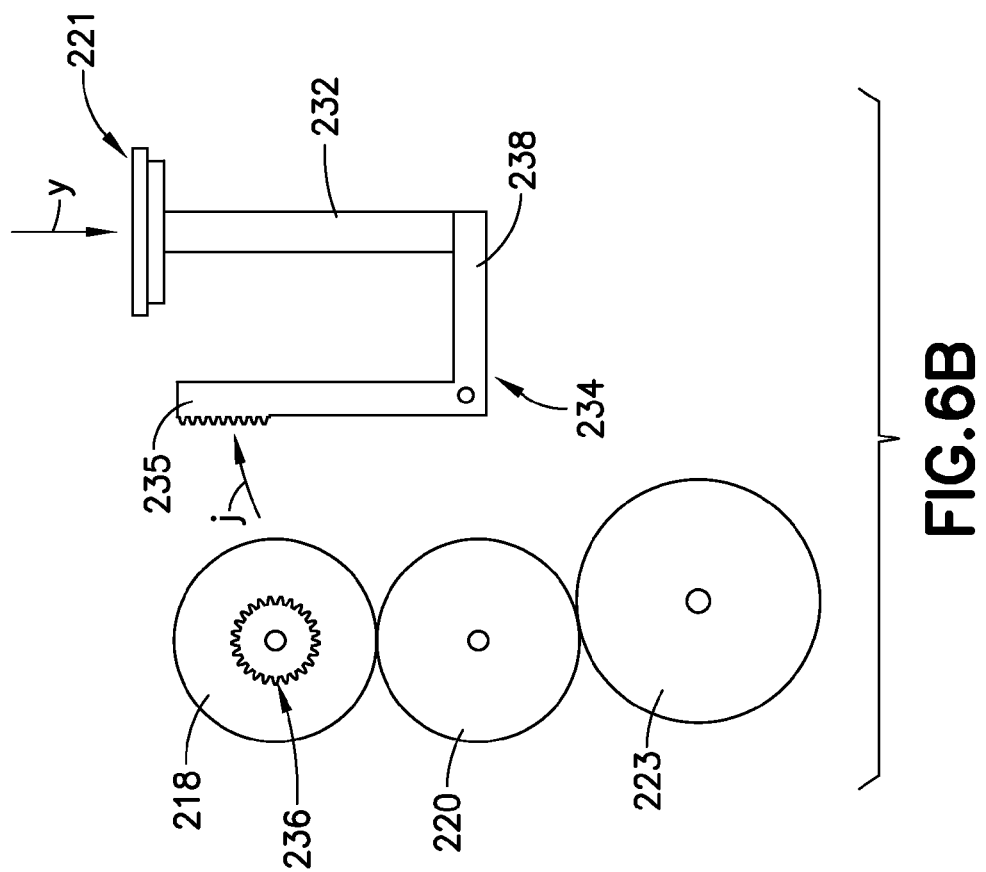
FIG. 6B is a schematic side view of the strip handling device as shown in FIG. 6A and in a second condition.

Each of rollers 218, 220, and 223 may include spindles 218a, 220a, and 223a, respectively, which may be mounted within housing 210 such that the rollers are rotatable but are otherwise in a fixed position relative to the housing. Locking mechanism 233 may include a pawl 234 including a rack 235, which is engageable with a pinion 236 that is operatively coupled to at least one of the rollers 218, 220, and 223. Actuator 221 transitions pawl 234 between a first position in which rack 235 is engaged with pinion 236 (FIG. 6A) and a second position in which the rack is not engaged with the pinion (FIG. 6B). When rack 235 is engaged with pinion 236, the teeth of the rack interact with the teeth of the pinion, thereby preventing rotation of the pinion. As shown in FIG. 5, pinion 236 may be secured to first roller 218 such that when the locking mechanism 233 is in a locked condition, rack 235 engages the first roller 218 and is prevented from rotating.

Pawl 234 may be biased toward an engaged position with respect to pinion 236 such that when actuator 221 is not actuated, the rotations of rollers 218, 220, and 223 are locked with respect to one another. Pawl 234 may include a spindle 239, which may be secured and mounted within housing 210 such that pawl 234 may be pivoted, but is otherwise fixed in position with respect to the housing. A torsion spring 237 may be disposed about spindle 239 of pawl 234, and may have a first end secured to the pawl, and a second end secured to housing 210. Torsion spring 237 may have a stored potential energy to bias rack 235 of pawl 234 in a radial direction toward pinion 236.

Figure 6A:
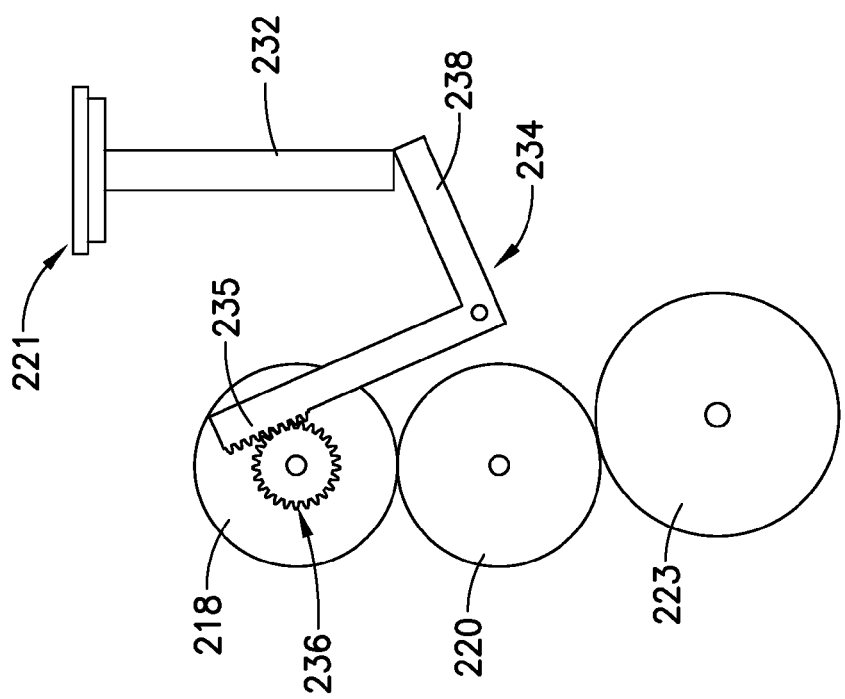
FIG. 6A is a schematic side view of the strip handing device shown with parts removed and in a first condition.

Pawl 234 may have a generally L-shaped configuration, and may include an arm member 238, which contacts a depressing member 232 extending longitudinally from actuator 221. When unactuated, rack 235 of pawl 234 is in contact with pinion 236, as shown in FIG. 6A. As shown in FIG. 6B, when actuator 221 is depressed, that is, moved in direction y, depressing member 232 engages arm member 238, and causes pawl 234 to pivot in direction j away from pinion 236, thereby allowing the rollers 218, 220, and 223 to rotate. When pawl 234 is pivoted such that rack 235 is moved away from pinion 236, spring 237 becomes more tightly wound.

When actuator 221 is no longer being depressed, pawl 234 pivots back to its initial position (FIG. 6A), rack 235 will automatically return to an engaged position with respect to pinion 236, thereby locking the rotation of rollers 218, 220, and 223 with respect to one another. Since first roller 218 is in frictional contact with second roller 220, which is in frictional contact with roller 223, the engagement of the pinion 236 by rack 235 prevents the rotation of all of the rollers 218, 220, and 223.

During use, an end of a strip S is brought into contact with the junction of first and second rollers 218, 220 such that when roller 223 rotates in direction B, the corresponding rotation of the first and second rollers will cause the strip to be drawn into inner compartment 212. Once an end of strip S is positioned between first and second rollers 218, 220, actuator 221 may be depressed. Depression of the actuator 221 causes the first and second rollers to rotate as discussed above, thereby drawing the strip into inner compartment 212. When inner compartment 212 is full of collected strips S, device 200 may be disposed of, along with the collected strips, or the inner compartment may be emptied and the device may be re-used.

Some embodiments of the present disclosure are further described in the paragraphs below.

Alternative Embodiment A

A test strip handling device, comprising:
a housing;
an inner compartment within the housing, the inner compartment having a space in which at least one item may be stored;
an opening in the housing, the opening being connected to the space of the inner compartment;
a first member; and
a second member,
wherein the first and second members are configured to securely receive the at least one item therebetween and to guide the at least one item through the opening and into the space of the inner compartment.

Alternative Embodiment B

The device of embodiment A, wherein the first and second members inhibit removal of the at least one item via the opening.

Alternative Embodiment C

The device of embodiment A, wherein the first member is a first roller and the second member is a second roller.

Alternative Embodiment D

The device of embodiment C, wherein the first roller has a generally cylindrical configuration and has a first axis extending lengthwise and the second roller has a generally cylindrical configuration and has a second axis extending lengthwise, the first axis and the second axis being generally parallel with respect to each other.

Alternative Embodiment E

The device of embodiment C, wherein the first and second rollers are rotatable relative to one another, rotation of the first and second rollers relative to one another, wherein the first and second rollers are configured to cause translation of the at least one item when the at least one item is positioned between the first and second rollers.

Alternative Embodiment F

The device of embodiment E, wherein the first roller is in contact with the second roller.

Alternative Embodiment G

The device of embodiment E, wherein counter-clockwise rotation of the first roller and clockwise rotation of the second roller causes translation of the at least one item in a direction toward the space of the inner compartment when the at least one item is positioned between the first and second rollers.

Alternative Embodiment H

The device of embodiment C, further comprising an energy storage device configured to bias the first and second rollers to rotate relative to one another.

Alternative Embodiment I

The device of embodiment H, wherein the energy storage device comprises:
a third roller;
a spring; and
a locking mechanism transitionable between a locked state and an unlocked state,
wherein rotation of the third roller in a first direction causes the spring to wind and store potential energy, and wherein when the locking mechanism is in the locked state, the spring is prevented from unwinding, and when the locking mechanism is in the unlocked state, the spring unwinds to convert the potential energy to kinetic energy which causes the first and second rollers to rotate relative to one another.

Alternative Embodiment J

The device of embodiment I, wherein the locking mechanism includes a pinion operatively coupled to at least one of the first and second rollers, and a rack configured to engage the pinion when in the locked state and to be disengaged from the pinion when in the unlocked state.

Alternative Embodiment K

The device of embodiment C, further comprising: an actuator configured to cause rotation of the first and second rollers relative to one another.

Alternative Embodiment L

The device of embodiment A, further comprising:
a door formed in the housing through which the at least one item may be removed from the inner compartment.

Alternative Embodiment M

The device of embodiment A, further comprising:
a guide channel configured to receive the at least one item therethrough in a direction toward the space of the inner compartment.

It will be appreciated that various features set forth in the embodiments discussed herein can be combined in different ways than presented herein. It will also be appreciated that the features described in connection with individual embodiments may be shared with other embodiments discussed herein.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as detailed by the following claims.

The invention claimed is:

1. A test strip handling device, comprising:
a housing having an external opening;
an interior compartment disposed within the housing, the interior compartment having a space configured to store at least one test strip, the at least one test strip including a reagent adapted to react with an analyte in a fluid sample and to produce a reaction indicative of the concentration of the analyte in the fluid sample;
first and second members positioned adjacent one another within the housing, and
an energy storage device including a third member frictionally engaged with one of the first and second members and configured to rotate in a first direction to store energy and to bias the first and second members to move relative to one another upon release of the stored energy,
wherein the first and second members are constructed and arranged to receive the at least one test strip there between and to guide the at least one test strip from the opening into the space of the interior compartment.

2. The device of claim 1, wherein when the at least one test strip is stored within the interior compartment, the first and second members inhibit removal of the at least one test strip through the opening.

3. The device of claim 1, wherein the first member is a first roller and the second member is a second roller.

4. The device of claim 3, wherein the first roller has a generally cylindrical configuration and has a first axis extending lengthwise and the second roller has a generally cylindrical configuration and has a second axis extending lengthwise, the first axis and the second axis being generally parallel with respect to each other.

5. The device of claim 3, wherein the first and second rollers are rotatable relative to one another, and wherein the first and second rollers are configured to cause translation of the at least one test strip when the at least one test strip is positioned between the first and second rollers.

6. The device of claim 5, wherein the first roller is in contact with the second roller.

7. The device of claim 5, wherein the first roller and the second roller are spaced apart from one another, such that a gap is created there between, the gap sized to receive a test strip therein.

8. The device of claim 5, wherein counter-clockwise rotation of the first roller and clockwise rotation of the second roller causes translation of the at least one test strip in a direction toward the space of the inner compartment when the at least one test strip is positioned between the first and second rollers.

9. The device of claim 3, wherein the energy storage device is configured to bias the first and second rollers to rotate relative to one another.

10. The device of claim 9, wherein the third member is a third roller and the energy storage device further includes:
a spring; and
a locking mechanism transitionable between a locked state and an unlocked state,
wherein rotation of the third roller in the first direction causes the spring to wind and store potential energy, and
wherein when the locking mechanism is in the locked state, the spring is prevented from unwinding, and when the locking mechanism is in the unlocked state, the spring unwinds to convert the potential energy to kinetic energy which causes the first and second rollers to rotate relative to one another.

11. The device of claim 10, wherein the locking mechanism includes a pinion operatively coupled to at least one of the first and second rollers, and a rack configured to engage the pinion when in the locked state and to be disengaged from the pinion when in the unlocked state.

12. The device of claim 3, further comprising:
an actuator configured to cause rotation of the first and second rollers relative to one another.

13. The device of claim 1, further comprising:
a guide channel configured to receive the at least one test strip therethrough in a direction toward the space of the interior compartment.

14. A test strip handling device, comprising:
a housing;
an interior compartment disposed within the housing, the interior compartment having a space configured to store at least one test strip, the at least one test strip including a reagent adapted to react with an analyte in a fluid sample and to produce a reaction indicative of the concentration of the analyte in the fluid sample; and first and second rollers positioned adjacent one another within the housing and capable of rotating relative to one another, an energy storage device including a third roller frictionally engaged with one of the first and second rollers and configured to rotate in a first direction to store energy and to bias the first and second rollers to rotate relative to one another upon release of the stored energy, wherein when the at least one test strip is positioned adjacent the first and second rollers, counter-clockwise rotation of the first roller and clockwise rotation of the second roller causes translation of the at least one test strip in a direction toward the space of the interior compartment.

15. The device of claim 14, wherein the first roller has a generally cylindrical configuration and has a first axis extending lengthwise and the second roller has a generally cylindrical configuration and has a second axis extending lengthwise, the first axis and the second axis being generally parallel with respect to each other.

16. The device of claim 15, wherein the first roller is in contact with the second roller.

17. The device of claim 15, wherein the first roller and the second roller are spaced apart from one another, such that a gap is created there between, the gap sized to receive the test strip therein.

18. The device of claim 15, wherein the energy storage device further includes:

a spring; and a locking mechanism transitionable between a locked state and an unlocked state, wherein rotation of the third roller in the first direction causes the spring to wind and store potential energy, and wherein when the locking mechanism is in the locked state, the spring is prevented from unwinding, and when the locking mechanism is in the unlocked state, the spring unwinds to convert the potential energy to kinetic energy which causes the first and second rollers to rotate relative to one another.

19. A method of storing a test strip, comprising:

placing an end of the test strip into an opening of a test strip handling device, the test strip including a reagent adapted to react with an analyte in a fluid sample and to produce a reaction indicative of the concentration of analyte in the fluid sample;

positioning the test strip at the junction between first and second rollers housed within the test strip handling device, such that the test strip is positioned adjacent the first and second rollers;

rotating a third roller to store energy to be used to cause the first and second rollers to rotate upon actuation;

actuating the first roller to rotate in a first direction and the second roller to rotate in a second direction, wherein the second direction is opposite the first direction; and drawing the test strip into an interior compartment of the test strip handling device while the first and second rollers are rotating.

20. The method of claim 19, wherein the step of rotating occurs before the step of placing.

* * * * *